United States Patent [19]
Accisano, III

[11] Patent Number: 5,571,085
[45] Date of Patent: Nov. 5, 1996

[54] STEERABLE OPEN LUMEN CATHETER

[75] Inventor: Nicholas G. Accisano, III, Howell, N.J.

[73] Assignee: Electro-Catheter Corporation, Rahway, N.J.

[21] Appl. No.: 410,238

[22] Filed: Mar. 24, 1995

[51] Int. Cl.$^6$ ..................................................... A61M 37/00
[52] U.S. Cl. ........................... 604/95; 604/281; 128/772; 128/657
[58] Field of Search ............................ 604/95, 281, 164; 128/656–658, 772, 4

[56] References Cited

U.S. PATENT DOCUMENTS

| | | |
|---|---|---|
| 3,625,200 | 12/1971 | Muller . |
| 3,854,473 | 12/1974 | Matsuo . |
| 4,169,464 | 10/1979 | Obrez . |
| 4,474,174 | 10/1984 | Petruzzi . |
| 4,757,827 | 7/1988 | Buchbinder et al. . |
| 4,799,496 | 1/1989 | Hargreaves et al. . |
| 4,830,023 | 5/1989 | de Toledo et al. . |
| 4,886,067 | 12/1989 | Palermo . |
| 4,940,062 | 7/1990 | Hampton et al. . |
| 4,955,382 | 9/1990 | Franz et al. . |
| 4,979,510 | 12/1990 | Franz et al. . |
| 4,998,916 | 3/1991 | Hammerslag et al. . |
| 5,030,204 | 7/1991 | Badger et al. . |
| 5,060,660 | 10/1991 | Gambale et al. . |
| 5,114,402 | 5/1992 | McCoy . |
| 5,190,050 | 3/1993 | Nitzche . |
| 5,254,088 | 10/1993 | Lundquist et al. . |
| 5,257,451 | 11/1993 | Edwards et al. . |
| 5,269,757 | 12/1993 | Fagan et al. . |
| 5,273,535 | 12/1993 | Edwards et al. . |
| 5,275,162 | 1/1994 | Edwards et al. . |
| 5,281,212 | 1/1994 | Savage et al. . |
| 5,281,217 | 1/1994 | Edwards et al. . |
| 5,293,869 | 3/1994 | Edwards et al. . |
| 5,308,910 | 5/1994 | Edwards et al. . |
| 5,313,943 | 5/1994 | Houser et al. . |
| 5,314,466 | 5/1994 | Stern et al. . |
| 5,318,525 | 6/1994 | West et al. . |
| 5,358,479 | 10/1994 | Wilson . |
| 5,368,564 | 11/1994 | Savage . |
| 5,472,017 | 12/1995 | Kovalcheck . |

*Primary Examiner*—Randall L. Green
*Assistant Examiner*—Perry E. VanOver
*Attorney, Agent, or Firm*—Cohen, Pontani, Lieberman, Pavane

[57] ABSTRACT

A steerable catheter includes a handle and a catheter tube, the distal region of which may be selectively curved by the operator. A fluid transport tube extends the entire length of the catheter to enable a user to supply or extract fluids from a patient through the catheter. Within the distal tip portion of the catheter tube, two support members are affixed to opposite sides of the fluid transport tube. The distal end of the tip portion of the catheter tube is attached to at least one and preferably two pull cables. When a pull cable is tightened, the catheter's tip portion assumes a curve defined by the orientation in which the support members are affixed to the fluid transport tube. The two support members allow the tip portion of the catheter tube to assume a curvature only in a direction that is perpendicular to the plane of the two support members.

27 Claims, 9 Drawing Sheets

STEERABLE OPEN LUMEN CATHETER

FIELD OF THE INVENTION

The present invention relates to vascular catheters for use in medical procedures and, more particularly, to catheters that can be remotely guided or steered by selective deflection of the catheter distal end or tip.

BACKGROUND OF THE INVENTION

Catheters have been in common use in medical practice for many years. They are often used, for example, to probe locations inside a body or a patient which are otherwise unreachable without surgery. A catheter is first inserted into a vein, artery, or other structure or region of the body of the patient. The catheter is then guided to the area of concern by further inserting it into the patient's body. As medical knowledge increases, more uses of catheters have been developed and these uses have become more complex so that the ability to accurately and selectively steer the distal portion of the catheter has become of extreme importance. For example, there is a need to use steerable catheters to supply or remove fluids or cells to or from various internal tissues of the patient and to apply or sense electrical signals to or from such tissues. Administered fluids may, for example, be in the form of a liquid, suspension or gel containing a drug or other chemical used, for example, to treat or anesthetize the tissue.

In order to place the tip of the catheter in the correct location and position, it is often necessary or highly desirable to variously curve the catheter so that its distal portion will travel into the proper anatomical region as the catheter is inserted into the patient. After the distal portion has been so curved, it is also often desirable to rotate the catheter while maintaining the curvature of the distal region so that the intended portion of the catheter can then approach and/or contact the particular tissue of interest. It is also important that the catheter be able to make firm contact with the tissue of interest to facilitate reliable application or removal of fluid by the catheter and/or reliable transmission or sensing of an electrical current to or from the tissue.

A catheter which addresses some of the above problems is disclosed in U.S. Pat. No. 5,190,050, the entire disclosure of which is expressly incorporated by reference herein. In the catheter disclosed therein, the distal portion easily and reliably bends or twists in an angular orientation or curve that is selectively controllable. The distal end of the catheter is hollow and has at least two flat planar rigid juxtaposed shims mounted therein. The distal ends of the shims are attached to one another while the proximal end of at least one of the shims is attached to a pull cable and ultimately to the catheter handle. When a doctor or other user manipulates the catheter handle so that the catheter translates distally with respect to the handle, one of the shims follows the distal translation while the other shim retains its longitudinal distance from the handle causing the other shim and the associated distal portion of the catheter to longitudinally bend. Because of the planar shape of the shims and their rigidity, the bending of the distal portion of the catheter is always identical in direction, although varying in degree proportionally to the magnitude of the manipulation of the catheter handle, and is in a single plane of movement. The distal portion of the catheter can also optionally carry contact electrodes to transmit electrical pulses to or from tissue of the patient's body or can be made to pump fluids into or out of the body of the patient.

Although the catheter disclosed in U.S. Pat. No. 5,190,050 is reliable, completely functional and useful for many applications, the location of the shims and associated support structure between the shims and catheter handle within the hollow distal portion of the catheter results in contact between fluid flowing through the catheter and the shims and associated support structure. Depending on the construction material of the shims and support structure, and the properties of the fluid, such contact might in some cases introduce impurities into the fluid. This would be undesirable if fluid is being extracted from the patient through the catheter for laboratory testing, or if fluids are being delivered to the patient through the catheter such, for example, as medication, or liquids, suspensions, gels or gases containing a drug or other chemicals as may be used to treat or anesthetize the tissue. Additionally, such fluids could perhaps damage the shims and associated support structure, as by corrosion or clogging.

There are certain internal passages or chambers in the body which are not easily accessible to a catheter that can bend in only one plane. In the heart, for example, when it is desired to apply electrical pulses to or to introduce or extract fluids to or from the mitral or tricuspid valve annulus the tip of a catheter must be curved in two planes in order to properly contact the desired tissue. When the steerable catheter disclosed in U.S. Pat. No. 5,190,050 is used for this particular application, a doctor typically introduces the tip of the catheter into the heart's atrium and adjusts the catheter's handle to cause the tip to deflect in its single plane of deflection. The distal portion of the catheter's tip is then manipulated, either by rotation, by further insertion, or by a combination of both so that it contacts and is wedged against certain tissues and/or tissue walls within the heart. As a result, a proximal portion of the tip of the catheter, which does not contain the sandwiched juxtaposed rigid shims, is caused through such contact or abutment with tissue walls to assume a curve or bend in a plane that is different from the deflection plane of the distal end of the catheter's tip. As a result of this double twist in the catheter's tip, the catheter can then be further inserted so that it enters the mitral or tricuspid valve annulus. The second twist in the tip of the catheter, however, is not fixed or locked, is not readily controllable or selectively attainable, and is not pre-programmed into the catheter. As a consequence, the catheter tip manipulations needed to attain the desired catheter tip shape require substantial experience and skill.

The bi-directional steerable catheter disclosed in U.S. patent application Ser. No. 08/259,390, filed Jun. 14, 1994, the entire disclosure of which is expressly incorporated by reference herein, employs a single planar shim, the distal end of which is attached to two pull cables, one disposed on each side of the shim. When one pull cable is pulled, the other is correspondingly loosened, thereby causing the tip of the catheter to bend. The movement and curvature of the catheter's tip is selectively controlled by a user's manipulation of the catheter's handle. This catheter can thus bend in two directions in a single plane. The multiform twistable tip deflectable catheter disclosed in U.S. Pat. No. 5,358,479, the entire disclosure of which is expressly incorporated by reference herein, employs a single shim with at least one transverse or lateral twist which enables the tip of the catheter tube to assume a lockable pre-programmed curvature in more than one plane. Although the catheters disclosed in U.S. patent application Ser. No. 08/259,390 and in U.S. Pat. No. 5,358,479 are also reliable, completely functional and useful for many applications, if a fluid is to be transported through the catheter, chemical reactions between the fluid and the catheter's internal elements may occur which may reduce the effectiveness of the catheters or affect the purity of the fluids being transported through the catheter.

SUMMARY OF THE INVENTION

The steerable open lumen catheter of the present invention is directed to a catheter, the distal tip portion of which may be easily, reliably, selectively and remotely manipulated or bent and locked into a curved condition using an attached proximally disposed handle. In particular, the steerable open lumen catheter of the present invention also has an open lumen extending its entire length which enables a user to supply or extract fluids from the patient through the catheter. The catheter of the present invention comprises three primary portions: a catheter handle, a hollow catheter tube, and the tip of the catheter tube.

A fluid transport tube extends longitudinally through the entire catheter, from the handle through the catheter tube and through the tip of the catheter tube. The fluid transport tube is an elongated tube with a central lumen through which fluids can freely flow. Within the distal portion of the hollow catheter tube, two support members, preferably formed as metal wires, are affixed to opposite sides of the fluid transport tube along the portion of the fluid transport tube. The distal end of the tip portion of the catheter tube is attached to one and preferably two pull cables. If two pull cables are used, they are disposed on diametrically opposite sides of the fluid transport tube at the catheter tube's distal end. A guidewire spring surrounds the fluid transport tube and is disposed within the catheter tube from the catheter handle to the proximal end of the catheter's tip portion. The guidewire spring is mechanically connected or fixed to the body of the catheter handle so that, during use of the catheter, the guidewire spring does not move, longitudinally or rotationally, relative to the body of the catheter handle and to the catheter tube. The proximal ends of the two support members are attached to the distal end of the guidewire spring.

No specific form or structural configuration or operational attributes of the catheter handle are required, so long as the handle is capable of providing the intended selective control of the one or two pull cables, depending, respectively, upon whether one or two pull cables are used.

When one of the pull cables is tightened by a user's operation of the handle, the other pull cable is loosened and the tip portion of the catheter tube assumes a curve that is defined by the orientation in which the support members are affixed to the fluid transport tube. In particular, the two support members allow the catheter's tip portion to assume a curvature only in a direction that is perpendicular to the plane of the two support members. By affixing the two support members to the fluid transport tube in various ways, preselected catheter tip curves comprising multiple connected curves of various radii in a single plane or curves in more than one plane can be achieved. If two pull cables are used, pulling the other pull cable straightens the tip portion of the catheter tube. If only one pull cable is used, the two support members are preferably pre-stressed so that after tension in the pull cable is released, the catheter's tip portion tends to curve in the opposite direction or at least to straighten itself.

The catheter support members can be pre-stressed by forming them with an initial curvature and then attaching them to the guidewire spring so that in their initial state the catheter's tip portion assumes a particular curvature.

If two pull cables are used, they can each be selectively pulled, and no elastic band or pre-stressing of the support members is required to straighten or restraighten the catheter's tip. Consequently, the ability of the catheter of the present invention to assume any desired curvature, including no curvature whatsoever, will neither diminish nor vary through use of the inventive catheter.

The catheter tube is hollow, containing within its central lumen the guidewire spring. The outer shell of the catheter tube is preferably formed of a relatively rigid material, preferably with a wire braid embedded therein. An unreinforced section of catheter tubing is fixedly attached to the distal end of the reinforced tube so as to form the selectively deflectable distal portion. The structure of the catheter tube and of the enclosed guidewire spring render the catheter tube sufficiently rigid as to reliably transmit the relative longitudinal movement imparted by manipulation of the catheter's handle to the shim in the catheter tube's distal region. Its relative rigidity further assures the ability to withstand column loading (which occurs upon insertion of the catheter tube into a patient) with little possibility that the catheter tube will buckle.

The entire catheter tube, including its distal tip portion, can be easily and reliably rotated along its longitudinal axis by appropriately rotating the catheter handle about their common longitudinal axis. The construction of the catheter tube, comprising its relatively rigid outer shell, its embedded wire braid and its guidewire spring, ensure that an axial rotation of the catheter handle reliably translates to an equal and gradually-effected axial rotation of the catheter tube's distal tip portion. In addition, the construction of the catheter's tip portion, comprising in particular the two support members affixed to the fluid transport tube, permits the entire distal tip portion to be rotated while still maintaining the exact user-selected curvature of the distal tip portion. Also, the structure of the steerable catheter of the present invention allows the catheter's distal tip portion to be pressed tightly against a patient's internal tissues by simply applying an appropriate longitudinal or rotative force to the catheter handle, even when the distal tip portion has been and remains curved.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference numerals delineate similar elements throughout the several views.

DETAILED DESCRIPTION OF THE PRESENTLY PREFERRED EMBODIMENTS

Figure 3:
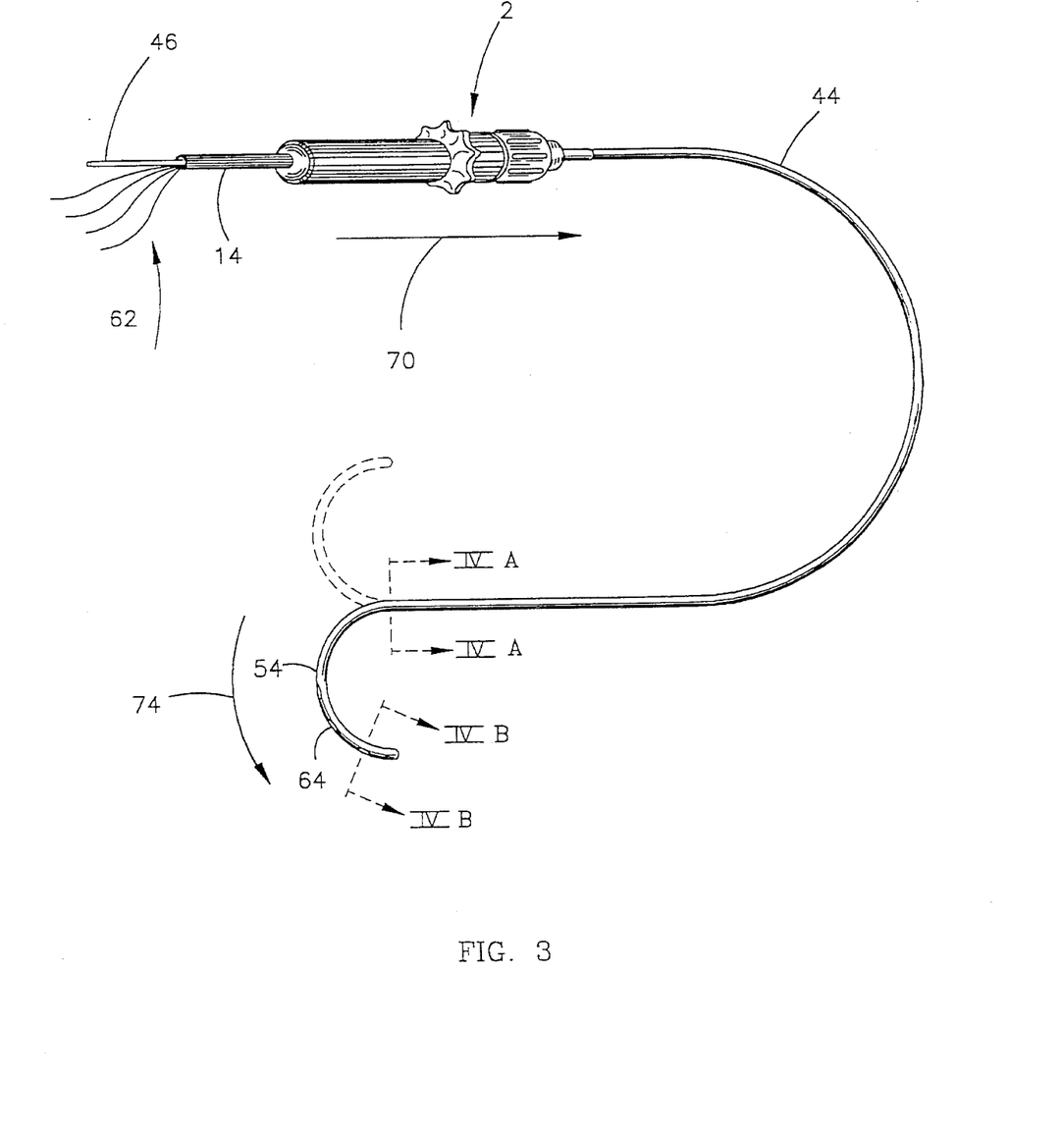
FIG. 3 is a simplified perspective drawing of a preferred embodiment of the entire steerable open lumen catheter of the present invention.

As shown in FIG. 3, the steerable open lumen catheter of the present invention broadly comprises a catheter handle 2, an elongated catheter tube 44, and the distal tip portion 54 of the catheter tube 44.

Figure 1:
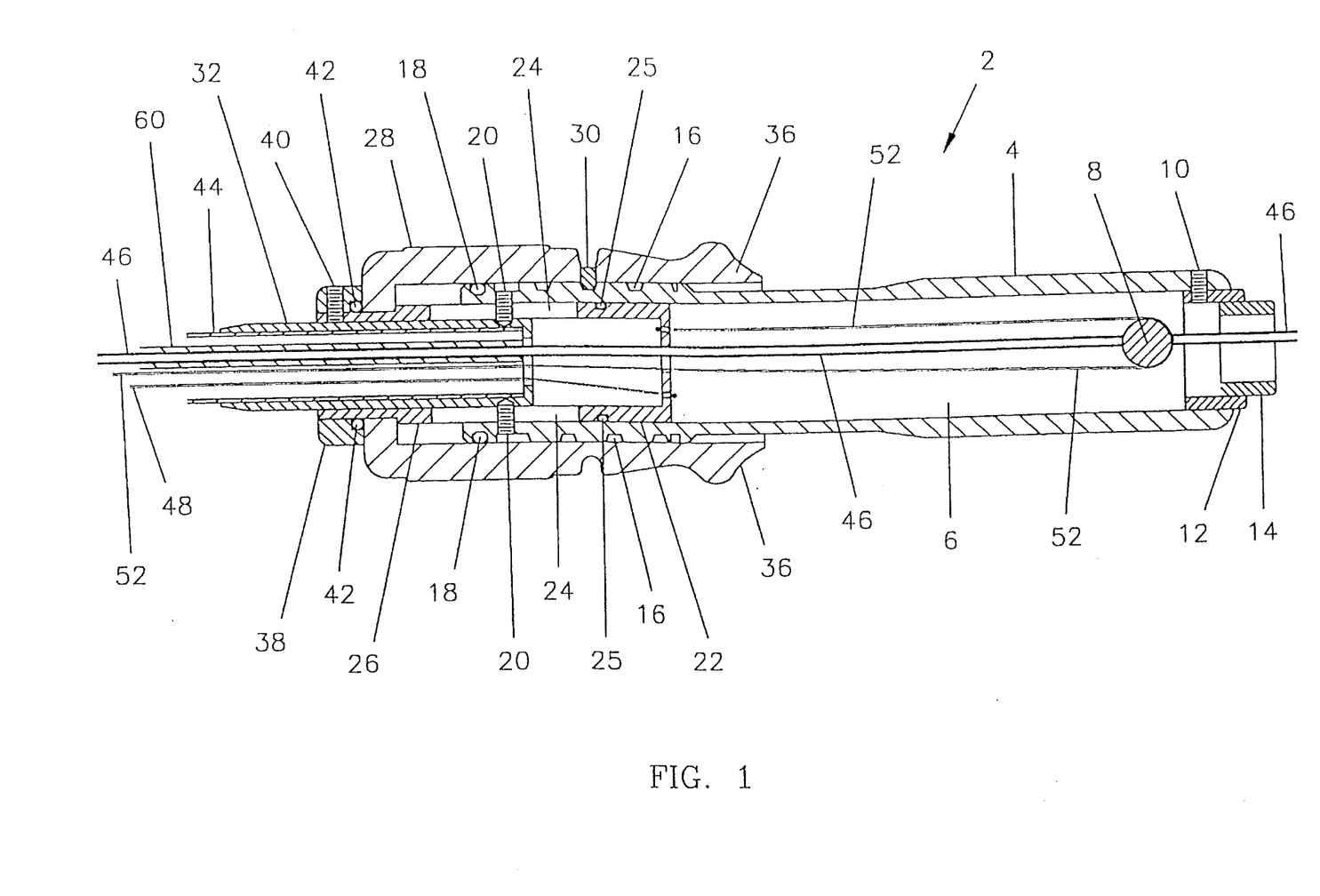
FIG. 1 is a longitudinal cross-sectional view of the handle portion of a preferred embodiment of the steerable open lumen catheter of the present invention.
Figure 2:
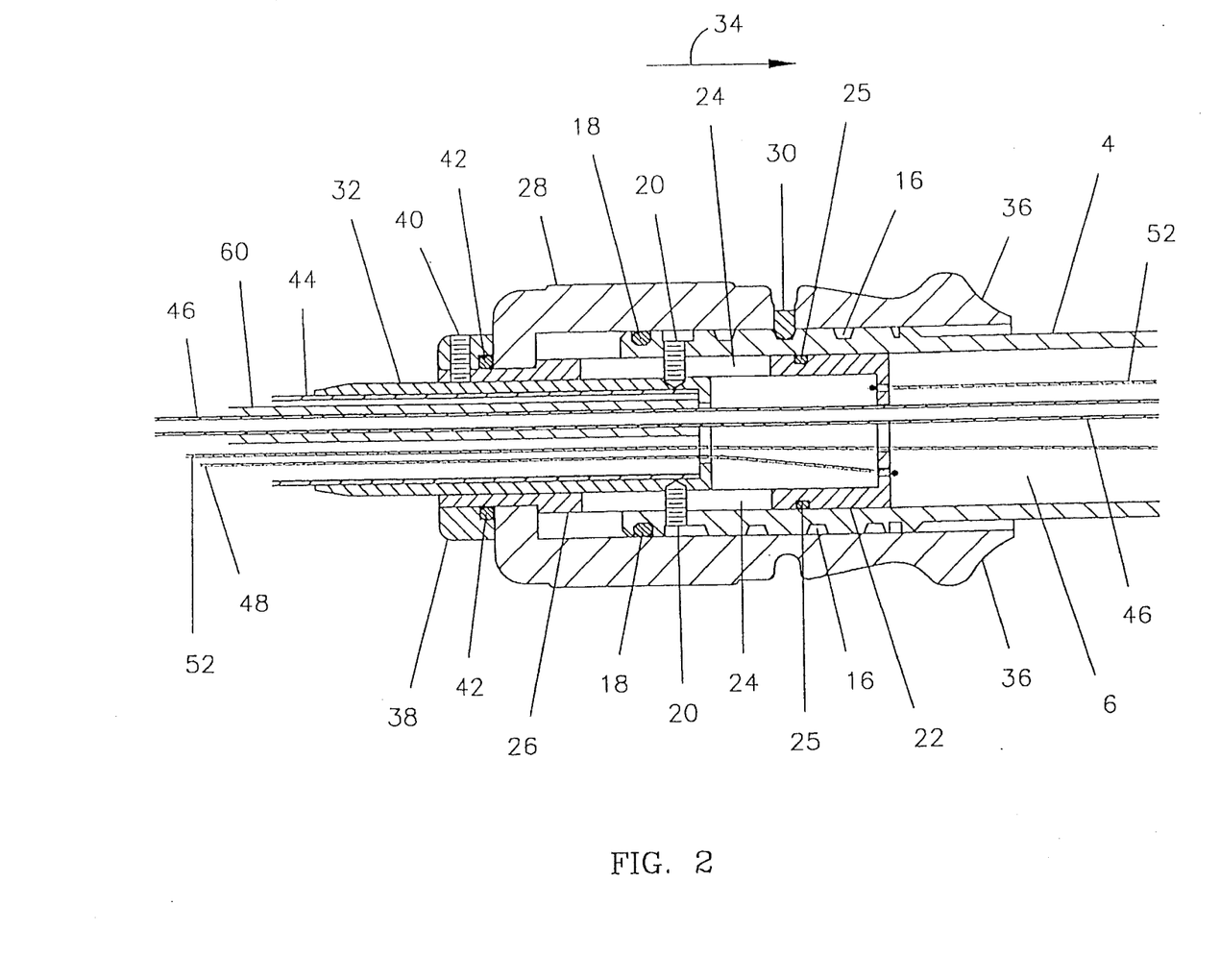
FIG. 2 is a detailed cross-sectional view of a portion of the handle portion of the preferred embodiment of the steerable open lumen catheter of the present invention shown in FIG. 1.

FIGS. 1 and 2 depict the handle portion of a preferred embodiment of a steerable catheter constructed in accordance with the present invention. The handle 2 of the catheter is comprised at its proximal end of a generally cylindrical body 4 having a central lumen 6 that extends longitudinally through and along the entire length of the body 4. At the proximal end of the body 4 (i.e. rightward in the Figures) are two lateral bores or holes. One hole passes entirely through the body 4 and through its central lumen 6. Within this first hole a pulley assembly 8 is securely mounted. The pulley assembly 8 may take the form of any kind of conventional device that changes the direction of a pulling force applied by or to a wire with minimal friction such, for example, as a pulley wheel rotatably mounted on a pin which is mounted in the hole at the proximal end of the body 4. The second hole passes from the outer surface of the body 4 to the central lumen 6 of the body 4. A set screw 10 is threadedly mounted in this second hole and functions to engage and securely mount a plug 12 within the proximal end of the central lumen 6 of the body 4. The plug 12 includes an aperture with which the set screw 10 engages. The plug 12 additionally has a longitudinally-oriented central lumen into which an end tube 14, also provided with a central lumen, is securely mounted. The body 4 is threaded near its forward or distal end (i.e. leftward in the Figures) with a helical thread 16 that circumscribes and corkscrews longitudinally along the outer surface of the body 4. Near the distal end of the body 4 is a third lateral bore or hole into which is threadedly mounted a pair of set screws 20, one from each side of the body 4. The holes in which the set screws 20 are received pass from the outer surface of the body 4 to the central lumen 6 of the body 4. A fourth lateral bore (not shown) is preferably cut into the body 4 so that it is perpendicular to the third bore. Similarly, a pair of set screws 20 are threadedly mounted into this fourth lateral bore. The distal end of the body has a circumferential groove into which is mounted an O-ring 18 formed of a suitably resilient material such as rubber or silicone. The O-ring 18 engages the inner surface of a collar sleeve 28, as described below.

A translation sleeve 22 is slidably mounted within the distal portion of the central lumen 6 of the body 4 so that a portion of the translation sleeve 22 extends beyond the distal end of the body 4. The translation sleeve 22 has a longitudinal central lumen that extends along its entire length. The central lumen of the translation sleeve 22 is closed off at its proximal end with a cap portion that has at least four holes. An O-ring, formed of a suitably resilient material such as rubber or silicone, is mounted into a circumferential groove cut into the translation sleeve 22 near its proximal end. O-ring 25 engages the inner surface of the body 4 to provide a frictional and sealing engagement between the body 4 and the translation sleeve 22. A longitudinal slot 24 proximate the center of the translation sleeve 22 extends laterally entirely through the translation sleeve 22. A second longitudinal slot (not shown) proximate the center of the translation sleeve 22 also extends laterally entirely through the translation sleeve 22 and perpendicular to the lateral slot 24. The translation sleeve 22 is positioned within the central lumen 6 of the body 4 so that the four set screws 20 engage and slide within and through the two longitudinal slots 24. The longitudinal slots 24 in the translation sleeve 22 are sufficiently wide that the four set screws 20 can slide therein with minimal friction. The forward or distal end portion of translation sleeve 22 is narrowed, forming a circumferential flange 26, and there is a lateral bore or hole defined in the forward, narrowed end of the translation sleeve 22 and passing from its outer surface to its central lumen.

A collar sleeve 28 is rotatably mounted onto the narrowed forward end of the translation sleeve 22 so that the collar sleeve 28 abuts the flange 26 of the translation sleeve 22. The collar sleeve 28 is roughly cylindrical in shape with a central, longitudinally oriented lumen. The collar sleeve 28 and its central lumen are shaped so that the collar sleeve 28 surrounds a portion of the forward or distal end of the translation sleeve 22 and the forward or distal end of the body 4, including the helical thread 16. A lateral bore is cut through collar sleeve 28, into which bore or slot is mounted a pin 30. Pin 30 extends through collar sleeve 28 so as to engage the helical thread 16 in the body 4. The rearward or proximal end of the collar sleeve 28 terminates in a flange portion 36.

Also mounted onto the narrowed forward or distal end of the translation sleeve 22 is an end collar 38 which is roughly annular in shape. The end collar 38 has a lateral bore or hole into which is mounted a set screw 40 that passes through the end collar 38 into the hole at the distal end of the translation sleeve 22 to thereby secure and removably mount the end collar 38 to the translation sleeve 22. The end collar 38 has an annular groove into which is fitted an O-ring 42 formed of a resilient material such as rubber or silicone. The O-ring 42 engages the distal end of the collar sleeve 28 and the outer surface of the translation sleeve 22.

A catheter base 32 is slidably mounted into the forward or distal end of the central lumen of the translation sleeve 22 and is secured therein only to body 4 by the set screws 20 which engage the outer surface of catheter base 32. Catheter base 32 is cylindrical in shape and has a central lumen which is capped at its proximal end with a cap that has at least one hole. The catheter tube 44 is securely fastened within the central lumen of catheter base 32, as by an adhesive bond or the like. The catheter base 32 is intended to minimize the effect upon the handle 2 and its constituent elements of any flexing of the proximal end of the catheter tube 44 during use of the catheter of the present invention. As discussed below with reference to FIGS. 3 through 8, the catheter tube 44 has a central lumen in which is disposed, among other elements, a guidewire spring 60, first and second pull cables 48, 52, a fluid transport tube 46, and a plurality of wire conductors 62.

The proximal end of the first pull cable 48 passes through the hole in the cap in the catheter base 32 and is secured to the cap of the translation sleeve 22, such as by passing the end of the first pull cable 48 through one of the four holes in the cap in the translation sleeve 22, and terminating the cable with an appropriate fitting.

The proximal end of the second pull cable 52 passes through the hole in the cap in the catheter base 32 and through a second of the four holes in the cap in the translation sleeve 22, around the pulley assembly 8 and back to the cap of the translation sleeve 22 where it is secured, such as by passing the end of the second pull cable 52 through a third of the four holes in the cap in the translation sleeve 22, and terminating the cable with an appropriate fitting. The hole in the cap of the translation sleeve 22 through which the second pull cable 52 passes without being secured is sized and shaped so that the second pull cable may freely slide therethrough with minimal friction. The pull cables 48, 52 are comprised of a material that is substantially or effectively nonstretchable when pulled or stressed longitudinally, such, for example, as the presently preferred stainless steel cable with a brass cladding and a teflon jacket with an overall diameter of about 0.010 inches.

The fluid transport tube 46 passes through the hole in the cap in the catheter base 32 and through a fourth of the four holes in the cap in the translation sleeve 22, past the pulley assembly 8 and out through the proximal end of the handle 2 through the end tube 14. The proximal end of the fluid transport tube 46 is preferably removably connected to a source of fluid or vacuum (not shown) which is used to pump fluid through the catheter into or out of the patient.

Referring now to FIG. 3, the catheter tube 44 has a length sufficient for it to be inserted into a patient's body lumen or cavity or the like so that the deflectable distal tip portion 54 of the catheter tube 44 can be controllably directed to and reach a particular point or location within the patient's body—as for example a location within the vascular system, such as the heart.

Figure 4:
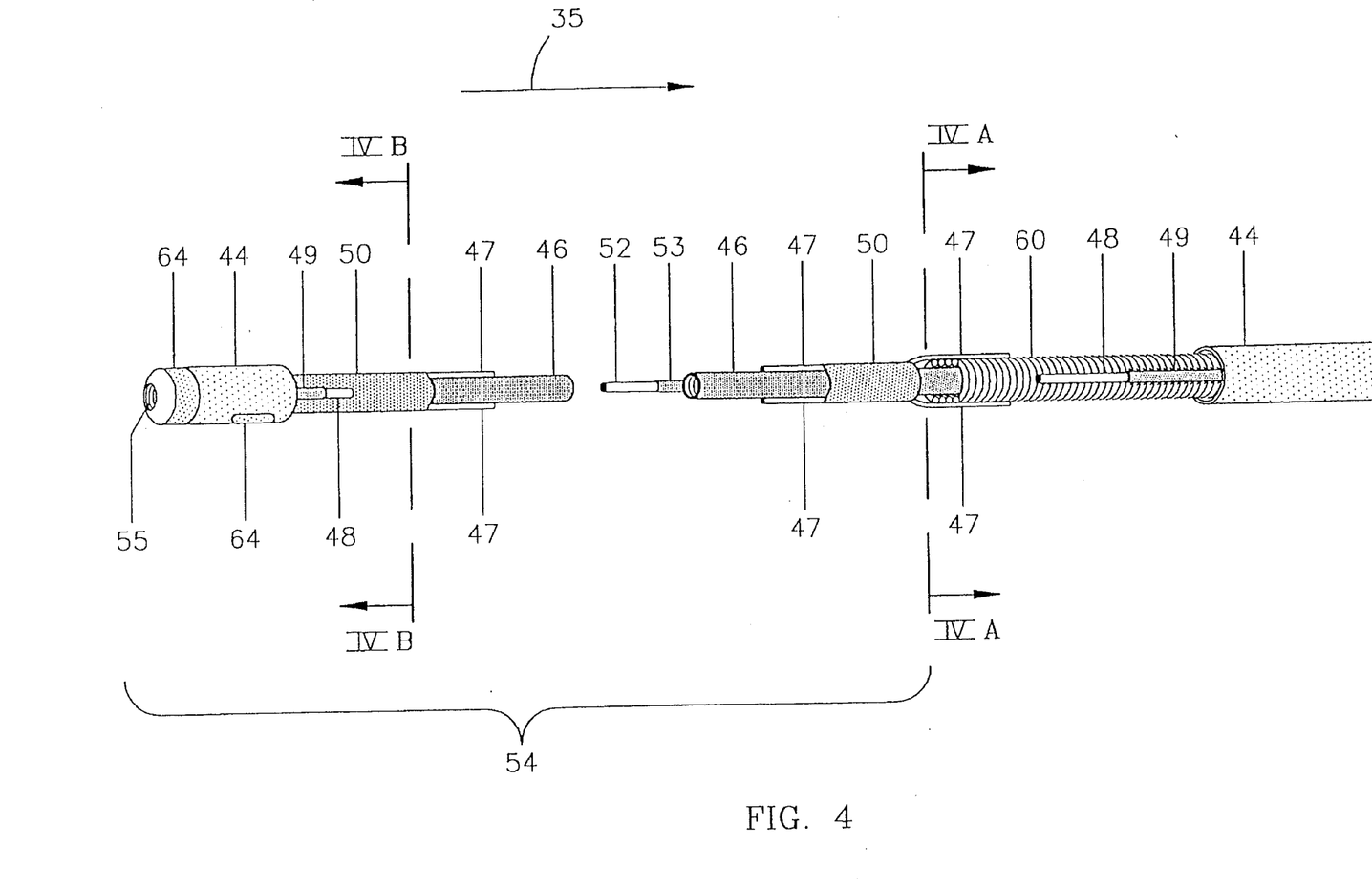
FIG. 4 is a perspective view of a first embodiment of the steerable open lumen catheter of the present invention with portions thereof proximate the catheter's tip portion partially broken away.
Figure 4A:
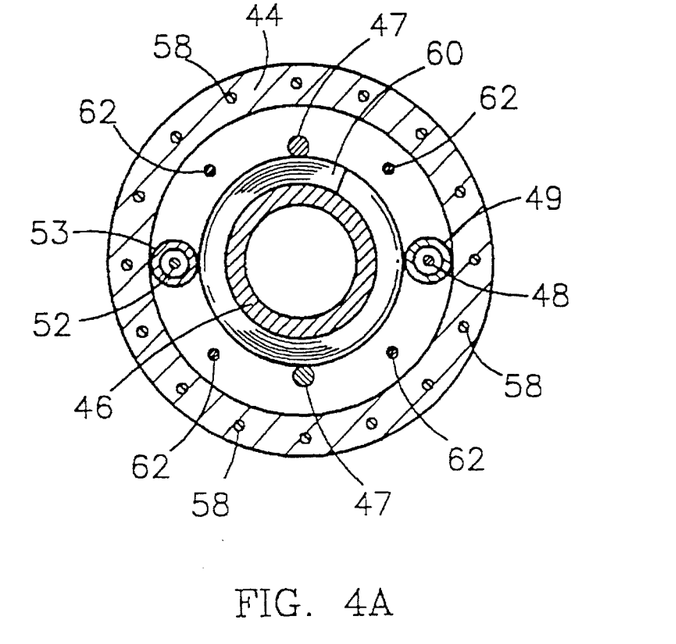
FIG. 4A is a cross-sectional view of the catheter tube taken along the lines IVA—IVA in FIG. 4.
Figure 4B:
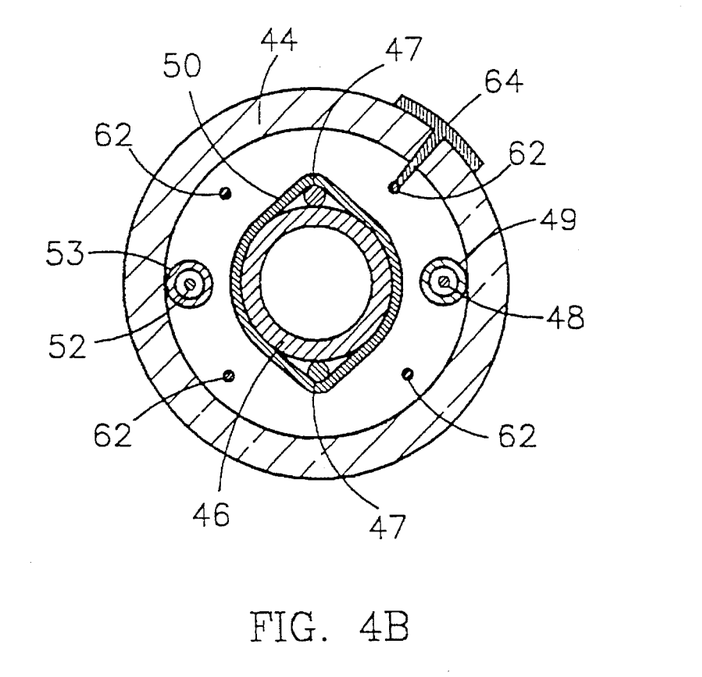
FIG. 4B is a cross-sectional view of the catheter tube taken along the lines IVB—IVB in FIG. 4.

Referring now to FIGS. 4, 4A and 4B, the catheter tube 44 is a hollow tube formed of a rigid material, preferably and by way of example a nylon co-polymer such as "Pebax" resin manufactured by ATOChem. The catheter tube 44 may also be comprised of any suitable plastic material and preferably has an outer diameter of about 0.092 inches, an inner diameter of about 0.066 inches, and a length of about 20 to 80 inches. In order to give the catheter tube 44 substantial effective rigidity and strength, it is preferred to include a wire braid 58 (as shown in FIG. 4A) embedded into the catheter tube 44, although the wire braid 58 may be eliminated. The wire braid 58 is preferably comprised of about 12 to 16 steel wires that are interwoven along the length of the catheter tube 44. The wire braid 58 may, alternatively, be comprised of more or less than 12 to 16 wires and the wires may, alternatively, be formed of a material other than steel such, illustratively, as fiberglass. The nylon co-polymer and wire braid 58 strengthen and support the structure of the catheter tube 44 in the same way as concrete and embedded metal reinforcement rods or bars, respectively, are used in building construction and are effective to transmit a torque applied to the handle by a user to the catheter's tip.

Disposed longitudinally within the central lumen of the catheter tube 44 is a guidewire spring 60 that provides columnar strength to the catheter tube 44. The size of the guidewire spring 60 is selected so that its outer diameter is slightly less than the inner diameter of the catheter tube 44. The outer diameter of the guidewire spring 60 is preferably about 40 to 70% of the inner diameter of the catheter tube 44. In one currently preferred embodiment, the outer diameter of the guidewire spring 60 is about 0.052 inches while the inner diameter of the catheter tube 44 is about 0.066 inches. The guidewire spring 60 is implemented as a long, tightly wound spring, preferably with a 0.012 inch pitch, and is disposed within and along almost the entire length of the catheter tube 44, extending from the rearward or proximal end of the catheter base 32 to the rearward or proximal end of the distal tip portion 54 of the catheter tube 44. The catheter tip portion 54 is the distal portion of the catheter tube 44 extending distally from the distal end of the guidewire spring 60.

An insulating sheath (not shown) preferably surrounds the guidewire spring 60 and extends from the catheter's distal portion 54 into the catheter handle 2. The insulating sheath electrically insulates the guidewire spring 60 from a plurality of insulated electrical wire conductors 62 disposed in the elongated annular space defined between the catheter tube 44 and the insulating sheath. The electrical conductors 62 may, for example, also have peripheral coatings that electrically insulate the electrical conductors 62 one from another and from the guidewire spring 60.

As shown in FIG. 4B, one end of each of the electrical conductors 62 passes to a respective electrical contact plate 64 that is integrally carried on the outer surface of the outer shell 56 at or along the distal portion 54 of the catheter tube 44. One such electrical contact plate 64 is preferably disposed at the distal portion 54 of the catheter tube 44 as shown in FIGS. 3 and 4. The electrical conductors 62 pass through the entire length of the catheter tube 44, through the central lumen in handle 2, and through and out of the end tube 14 where they may be separately connected to signal sensors (not shown) or to an electrical power source (not shown) that is operable to selectively sense or provide electrical pulses or signals from or to one or more of the conductors 62. The distal tip portion 54 of catheter tube 44 is preferably formed of relatively rigid material, as for example of the same resin family as is the outer shell of the proximal portion of catheter tube 44; however, the distal portion 54 may, alternatively, be comprised of a relatively lower durometer or "softer" material to increase its flexibility, so long as such material admits of firm attachment of the distal portion to the distal end of the proximally-disposed reinforced remainder of the catheter tube shell. In addition, it is preferred that the distal tip portion 54 not include an interior wire braid (as shown in FIG. 4B), thereby facilitating its selective bendability or deflection under a user's control and permitting the incorporation of the electrode pads 64.

Referring once more to FIG. 4, the fluid transport tube 46 is disposed within the central lumen of the guidewire spring 60 and extends through the catheter handle 2 and the central lumen of the guidewire spring 60 to the tip of the catheter terminating in a distal opening 55. Although a single distal opening 55 at the end of the catheter's tip portion 54 is shown, additional openings at the end of or along a length of the catheter's tip portion 54 may also be employed. The fluid transport tube 46 has a central lumen extending its entire length and is preferably made of a longitudinally rigid but laterally flexible material such, for example, as the presently preferred polyimide/braid/polyimide composite. The inner diameter of the fluid transport tube 46 is preferably sufficiently large to allow fluids and human cells to flow freely, preferably about 0.0394 inches, although the inner diameter can be larger or smaller depending upon the intended use of the catheter as discussed in detail below.

A pair of support members 47 are disposed along the outer surface of the fluid transport tube 46 along the portion of its length in the catheter's distal tip portion 54. In the embodiment shown in FIGS. 4 and 5, the support members are straight, generally cylindrical elongated wires or shims 47 and are disposed radially and symmetrically opposite one another along the fluid transport tube 46. As discussed in detail below with reference to the embodiments of the present invention shown in FIGS. 6 to 8, the support members 47 may alternatively be curved and/or disposed along the fluid transport tube 46 so that they are not radially opposite one another. The support members 47 are preferably comprised of stainless steel wire with a round cross-section and a diameter of about 0.010 inches. The support members 47 may alternatively have different cross-sectional diameters and shapes, such as, for example, elliptical, rectangular and triangular, and may be comprised of other materials provided that the cross-sectional shape and the composite materials provide the proper flexibility of the catheter's tip portion 54 as discussed in detail below with reference to the operation of the catheter of the present invention. The support members 47 preferable overlap the outer surface of the distal end of the guidewire spring 60 and are securely fastened, as by soldering, to the distal end of the guidewire spring 60. The support members extend to the distal end of the catheter tube 44.

Figure 5:
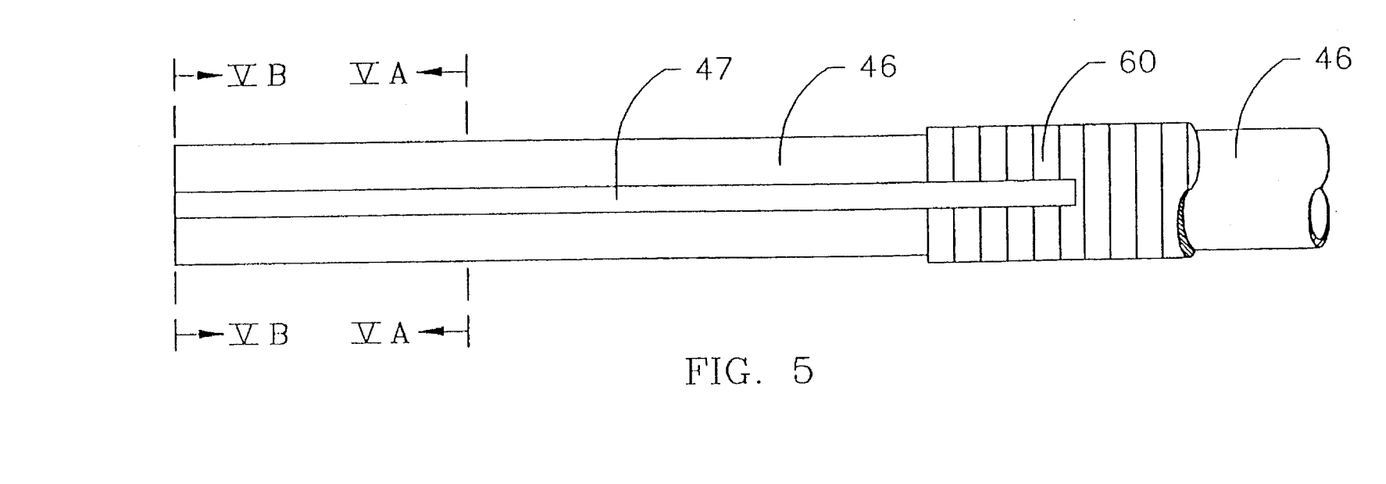
FIG. 5 is a simplified plan view of a portion of FIG. 4 showing the fluid transport tube, the guidewire spring and the support members of a first embodiment of the present invention.

The support members 47 are fixedly secured to the fluid transport tube 46 preferably by a bonding sleeve 50 that tightly envelopes the fluid transport tube 46 and the support members 47 in the catheter's tip portion 54. Alternatively, the support members 47 may be secured to the fluid transport tube 46 by a fixative or other conventional means. The bonding sleeve 50 thereby radially clamps the support members 47 against the outer surface of the fluid transport tube 46 and ensures that the circumferential positions of the support members 47 on the fluid transport tube 46 do not change during use of the catheter. The bonding sleeve is preferably formed of polyimide material with a thickness of about 0.0005 to 0.00075 inches. The bonding sleeve 50 may alternatively be employed only along a section of the catheter's tip portion 54, thereby leaving the support members 47 partially unsecured to the fluid transport tube 46. In this alternative embodiment, the section of the catheter's tip portion in which the support members 47 are unsecured is more flexible than the section in which the support members 47 are secured, thereby allowing this more flexible section to attain a tighter curvature.

The first and second pull cables 48, 52 are mounted along the outer surface of the guidewire spring 60 along its length within respective first and second guide tubes 49, 53. The guide tubes 49, 53 have inner diameters that are greater than the diameters of the pull cables 48, 52 and are preferably about 0.015 inches in diameter. The guide tubes 49, 53 are preferably made of a material, such, for example, as polyimide, which allows the pull cables 48, 52 to glide within their respective guide tubes 49, 53 with minimal friction. The first and second pull cables 48, 52, within their respective guide tubes 49, 53, extend from the catheter's handle 2 longitudinally within the catheter tube 44 through the catheter's tip portion 54 along the outer surface of the bonding sleeve 50 and are securely fastened within the distal end of the catheter's tip portion 54 on diametrically opposed sides. Although the guide tubes 49, 53 preferably extend from the rearward or proximal end of the catheter base 32 to the distal end of the tip portion 54 of the catheter tube 44, the guide tubes 49, 53 may alternatively extend from the rearward or proximal end of the catheter base 32 only to the distal end of the guidewire spring 60 or may even be eliminated in their entireties, provided that the material comprising the various elements directly contacting the pull cables 48, 52 allow the pull cables 48, 52 to slide in a longitudinal direction sufficiently freely within the catheter tube 44 during operation of the catheter. The catheter tube 44 is sized, molded or formed to hold the guide tubes 49, 53 securely against the outer surface of the guidewire spring 60 and against the outer surface of the bonding sleeve 50.

In FIGS. 4A and 4B, the first embodiment of the catheter of the present invention shown in FIG. 4 is depicted in cross-section taken along the lines IVA—IVA and IVB—IVB, respectively, in FIG. 4. The distal or forward end of the first and second pull cables 48, 52 pass on diametrically opposed sides of the fluid transport tube 46. Similarly, the two support members 47 are secured to diametrically opposed sides of the fluid transport tube 46. The wire conductors 62 are disposed between the catheter tube 44 and the guidewire spring 60, as shown in FIG. 4A, or between the catheter tube 44 and the bonding sleeve 50, as shown in FIG. 4B. An insulating sheath (not shown) may also be employed to envelope the guidewire spring 60 thereby electrically insulating it from the electrical conductors 62.

Figure 5A:
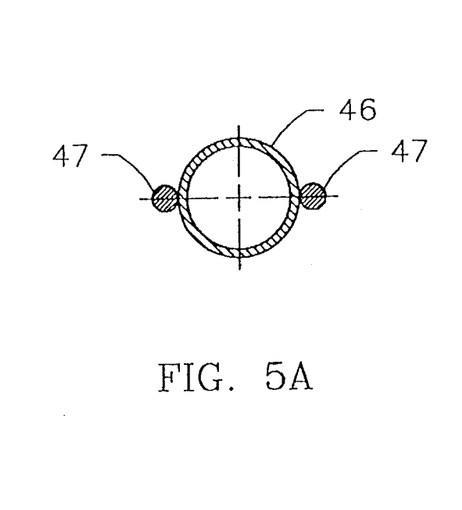
FIG. 5A is a cross-sectional view taken along the lines VA—VA in FIG. 5.
Figure 5B:
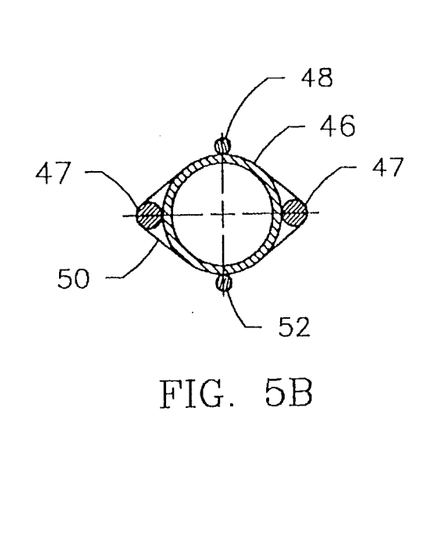
FIG. 5B is a cross-sectional view taken along the lines VB—VB in FIG. 5 and further including the bonding sleeve surrounding the fluid transport tube and the pull cables.

FIG. 5 depicts a simplified plan view of the proximal end of the catheter's tip portion 54 of the embodiment of the present invention depicted in FIG. 4. Simplified cross-sectional view of FIG. 5 are shown in FIGS. 5A and 5B. It can be seen that the two support members 47 are disposed on diametrically opposed sides of the fluid transport tube 46.

In operation, the catheter's distal tip portion 54 is first inserted into, for example, a patient. The location of the catheter's distal tip portion 54 within the patient is typically monitored non-invasively as, for example, through the use of X-rays or sonography or the like. When the distal tip portion 54 of the catheter tube 44 reaches a point in the body or vessel at which the distal tip portion 54 must be precisely steered or directed, as at a point where two vessels meet or within a chamber of the heart, the distal tip portion 54 can be selectively, remotely manipulated to assume a curved or bent shape, as shown in FIG. 3, from its normally straight, generally linear disposition by the doctor or operator through activation of the catheter tip deflector control mechanism in the handle 2. To effect such remote manipulation of the catheter's distal tip portion 54, the operator holds the rearward portion of the handle body 4 in one hand and slowly rotates, using the fingers of the same hand, the flange portion 36 of the collar sleeve 28, shown in FIGS. 1 and 2. As the collar sleeve 28 rotates, the pin 30 slides along the helical thread 16 thereby causing the collar sleeve 28 to be longitudinally displaced distally or proximally (depending upon the rotative direction of the collar sleeve 28) relative to the body 4. As the collar sleeve 28 moves longitudinally, so too do the attached end collar 38 and translation sleeve 22. However, because the catheter base 32 is firmly attached to the body 4 by the four set screws 20 that pass through the longitudinal slots 24 in the translation sleeve 22, the catheter base 32 does not move relative to the body 4 when the collar sleeve 28 moves longitudinally. Additionally, because the catheter tube 44 and the guidewire spring 60 are firmly attached to the catheter base 32, they are also immobile relative to the body 4. The longitudinal movement of the translation sleeve 22 causes the proximal ends of the first and second pull cables 48, 52 to move because they are attached to the cap of the translation sleeve 22. If, for example, the collar sleeve 28 is rotated so that it slides in the direction of the arrow 34 in FIG. 2, the translation sleeve 22 and its cap also slide in the direction of the arrow 34. The proximal end of the first pull cable 48 is likewise pulled in the direction of the arrow 34 by the translation sleeve 22, thereby tightening the first pull cable 48. The movement of the translation sleeve 22 also causes the proximal end of the second pull cable 52, which is attached to the cap of the translation sleeve 22, to move in the direction of the arrow 34. This movement is translated by the pulley assembly 8 to cause the second pull cable 52 to loosen or reduce its tension. At the distal tip portion 54 of the catheter tube 44, shown in FIG. 4, the movements described will cause the distal end of the first pull cable 48 to move in the direction of the arrow 35 and the distal end of the second pull cable 52 to move in the direction opposite that of the arrow 35. Consequently, and because the pull cables 48, 52 are attached at their distal ends to the distal end of the catheter tube 44, the first pull cable 48 is tightened while the second pull cable 52 is loosened. Because the two support members 47 are secured to the fluid transport tube 46 on diametrically opposite sides, the fluid transport tube 46 can bend only perpendicular to the plane defined by the two support members 47. Thus, the fluid transport tube 46 with the two support members 47 securely attached thereto bends in the same way as a flat planar elongated surface, i.e., it can only bend perpendicular to the planar surface. Consequently, as the first pull cable 48 is tightened and the second pull cable 52 is loosened, the fluid transport tube 46 bends in the preselected direction perpendicular to the plane defined by the two support members 47 and toward the viewer of FIG. 4. It will be appreciated from the foregoing that longitudinal movement of the collar sleeve 28 in the direction opposite to arrow 34 will similarly result in bending of the fluid transport tube 46, and thus of the catheter's distal tip portion 54, in a direction perpendicular to the plane defined by the two support members 47 and away from the viewer of FIG. 4. The amount of bending of the fluid transport tube 46 (and thus of the catheter distal portion 54) is dependent upon the amount of longitudinal displacement of the collar sleeve 28 relative to the body 4.

As a consequence of the securement of the support members 47 to the fluid transport tube 46, it is virtually impossible for the catheter's distal tip portion 54 to bend in normal use in any direction other than substantially perpendicular or lateral to the plane formed by the two support members 47. Additionally, the securement of the support members 47 to the fluid transport tube 46 also makes it virtually impossible for the catheter's distal tip portion 54 to bend out of the preprogrammed plane of curvature once a curvature has been selected.

Once a desired curvature in the catheter's distal portion 54 has been attained by appropriately rotating the collar sleeve 28 of the catheter's handle 2 in one direction, the curvature may be completely or partially removed or otherwise finely adjusted by rotating the collar sleeve 28 in the opposite direction. A curve of the catheter's distal tip portion 54 in the opposite direction (as shown in FIG. 3 in broken lines) can be obtained by thereafter continuing rotation of the collar sleeve 28 in this opposite direction of rotation.

Because the curvature in the catheter's distal tip portion 54 is achieved by rotating the collar sleeve 28 which, through the pin 30, engages the helical thread 16, the desired curvature, once attained, is easily preserved or locked simply by preventing the collar sleeve 28 from rotating relative to the handle body 4.

In use, it is often desirable to selectively rotate the entire catheter tube 44 through a desired angular adjustment after a desired curve in the distal tip portion 54 has been attained and locked in place. Such a rotation may be readily and reliably achieved by selectively rotating the entire handle 2, through manipulation of the handle body 4 together with the collar sleeve 28, about its longitudinal axis. The preferred rigidity and stability of the material and structure comprising the catheter tube 44 and the supporting structure of the guidewire spring 60 allow such axial rotation of the handle 2 to be smoothly, directly and reliably transmitted to the catheter's distal tip portion 54 with little risk of unintended or unanticipated sudden rotational movements or jolts. Thus, a given axial rotation of the handle 2 will result in a corresponding, substantially equal axial rotation of the catheter tube 44 and a corresponding, substantially equal rotation of its catheter's distal tip portion 54 (less any small rotational losses) while maintaining the locked curvature of the catheter's distal portion 54. Gradual axial rotations of the distal portion 54 of up to or exceeding 360° can therefore be reliably achieved without undue sensitivity or concern as to rotational position of the tip through simple rotation of the handle 2. Furthermore, the relatively rigid structure formed by the fluid transport tube 46 and its attached support members 47 is also effective to ensure reliable, steady rotation of the entire distal tip portion 54 without any sudden jolts of rotation while, at the same time, maintaining the locked curvature of the catheter's distal portion 54.

Finally, it should be recognized that the rigidity of the material and structure of the catheter tube 44 and the structure formed by the fluid transport tube 46 and its attached support members 47 allow the catheter tube 44 to be strenuously urged longitudinally in the distal direction indicated by the arrow 70, shown in FIG. 3, so as to firmly and aggressively press against and contact particular tissue within a patient's body, such as heart tissue, with reduced risk that the catheter tube 44 or its distal portion 54 will buckle or unexpectedly deform.

As will be appreciated from the foregoing description, the longitudinally-oriented lengths of the longitudinal slots 24 within the handle 2 are selected so that the set screws 20 limit the longitudinal movement of the translation sleeve 22 (and therefore of the collar sleeve 28 along the helical thread

16 cut into the body 4), thereby also defining the bounds or limitations of curvature of the distal tip portion 54 of the catheter tube 44. O-ring 18 ensures that the body 4 slides uniformly and tightly through the center lumen of the collar sleeve 28. O-ring 42 allows the end collar 38 to slide easily with and against the collar sleeve 28. O-ring 25 ensures that translation sleeve 22 slides uniformly and tightly through the center lumen of body 4.

In addition, the use of set screws 10, 20 and 40 and of pulley assembly 8 permits the handle to be readily assembled and disassembled for initial assembly, cleaning, adjustment or repairs, although it is contemplated that the commercial embodiment of the catheter of the present invention will be disposable.

Figure 6:
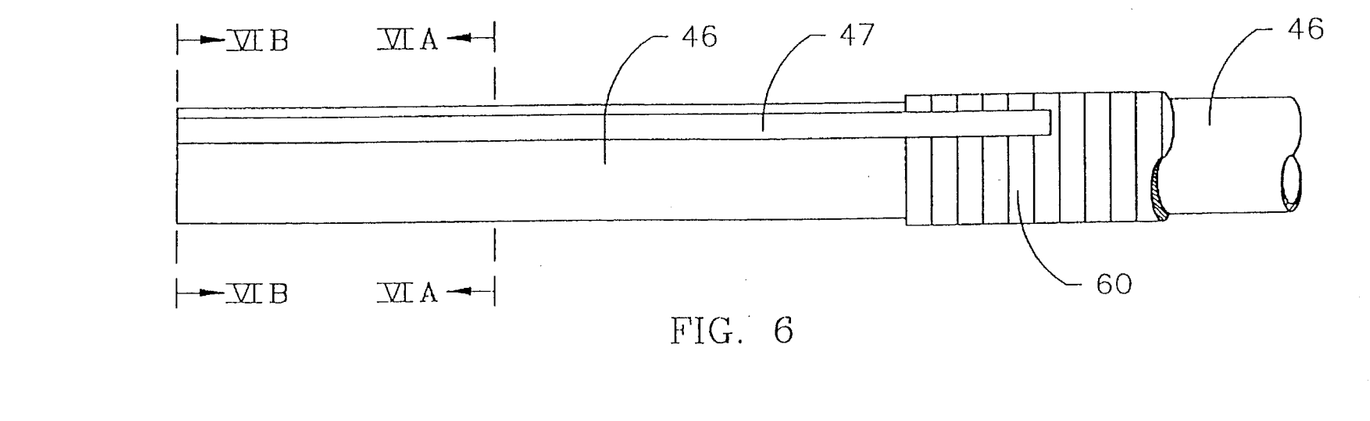
FIG. 6 is a simplified plan view similar to FIG. 5 showing the fluid transport tube, the guidewire spring and the support members of a second embodiment of the present invention.
Figure 6A:
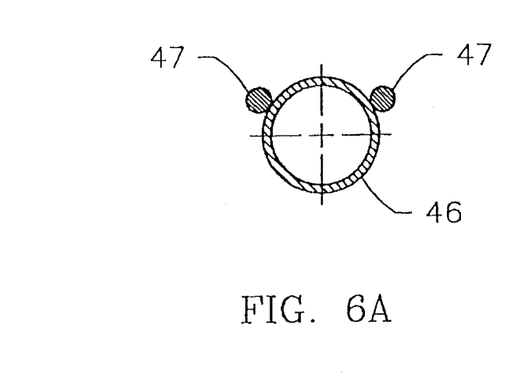
FIG. 6A is a cross-sectional view taken along the lines VIA—VIA in FIG. 6.
Figure 6B:
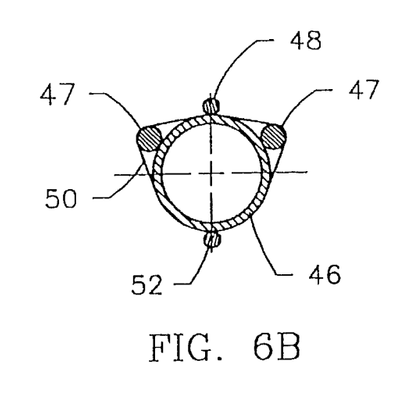
FIG. 6B is a cross-sectional view taken along the lines VIB—VIB in FIG. 6 and further including the bonding sleeve surrounding the fluid transport tube and the pull cables.

In the second embodiment of the present invention shown in FIGS. 6, 6A and 6B, the support members 47 are mounted symmetrically and in straight lines along the fluid transport tube 47 but off-centered and not radially opposite one another. As a consequence of this off-centered mounting of the support members 47, the fluid transport tube 47 will bend with less resistance in one direction than in the opposite direction, thereby resulting in different curvatures when the catheter's tip is deflected in opposite directions.

Figure 7:
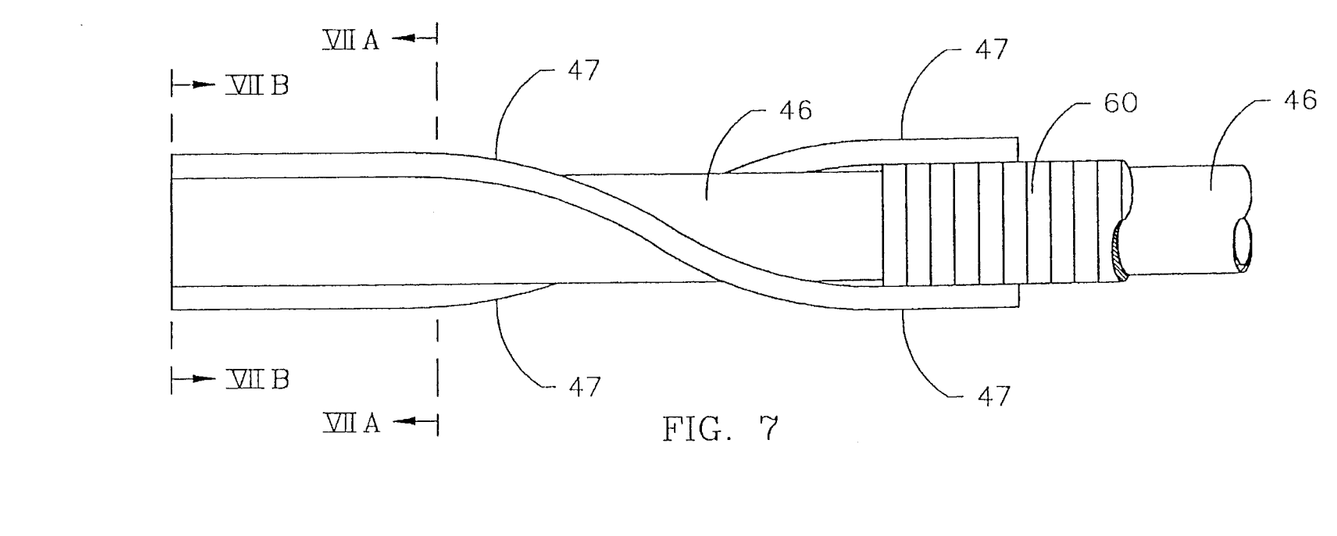
FIG. 7 is a simplified plan view similar to FIG. 5 showing the fluid transport tube, the guidewire spring and the support members of a third embodiment of the present invention.
Figure 7A:
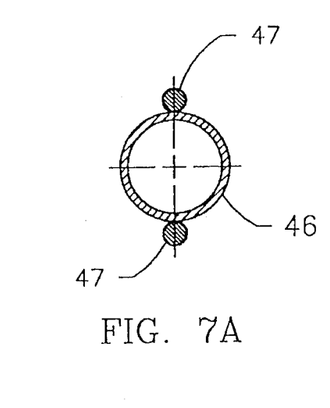
FIG. 7A is a cross-sectional view taken along the lines VIIA—VIIA in FIG. 7.
Figure 7B:
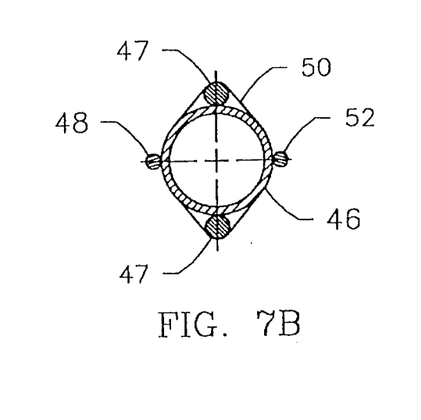
FIG. 7B is a cross-sectional view taken along the lines VIIB—VIIB in FIG. 7 and further including the bonding sleeve surrounding the fluid transport tube and the pull cables.

In the third embodiment of the present invention shown in FIGS. 7, 7A and 7B, the support members 47 are mounted symmetrically and centered along the fluid transport tube 47 but in a double helix. As a consequence of this centered double helix mounting of the support members 47, the fluid transport tube 47 will assume a three dimensional helix shape when one of the pull cables 48, 52 is tightened.

In the fourth embodiment of the present invention shown in FIGS. 8, 8A and 8B, the support members 47 are roughly S-shaped and are mounted symmetrically and in a curve along the fluid transport tube 47 so that the support members 47 are below center in the distal portion of the catheter tip, left in FIG. 8, but above center in the proximal portion of the catheter tip, right in FIG. 8. As a consequence of this mounting arrangement of the support members 47, the fluid transport tube 47 will bend in a single plane but with two curves of different radii when one of the pull cables 48, 52 is tightened due to the difference in curving resistance in the distal or left portion of the catheter's tip compared with the resistance in the proximal or right portion of the catheter's tip.

In the embodiments shown in FIGS. 5, 6, 7 and 8, the two pull cables 48, 52 are securely fastened at the distal end of the catheter's tip portion 54 on diametrically opposed sides so that only one pull cable is disposed on the circumference of the fluid transport tube 46 symmetrically between the two support members 47 as shown in FIGS. 5B, 6B, 7B and 8B. By positioning the pull cables 48, 52 equidistant between the two support wires 47 and only one pull cable between the support wires 47 along each circumferential arc of the fluid transport tube 46, tightening of one of the pull cables will maximize the proportion of the pulling force transmitted by the pull cable to cause the catheter's tip portion 54 to bend perpendicular to the plane formed by the two support members 47.

Although the embodiment of the present invention shown in FIGS. 1, 2, 4, 4A and 4B employ two pull cables 48, 52, a single pull cable may alternatively be used. In this embodiment, the support members 47 are preferably pre-stressed so that when tension applied to the catheter's tip portion is released by the single pull cable, the catheter's tip portion curves in the opposite direction and at least tends to straighten.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

Figure 8:
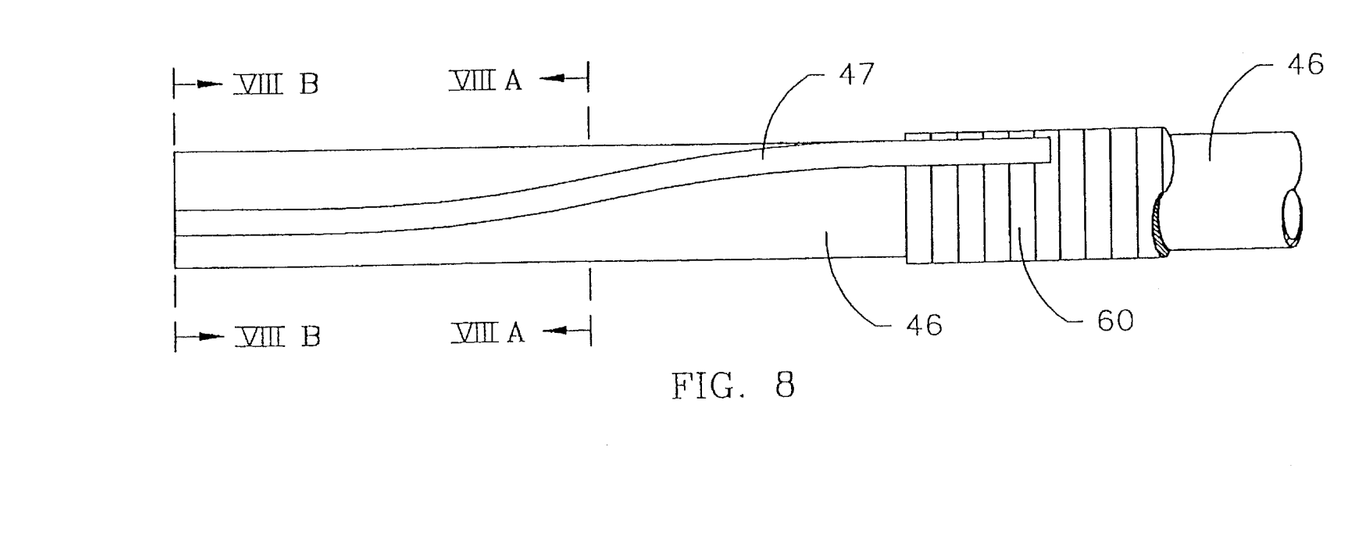
FIG. 8 is a simplified plan view similar to FIG. 5 showing the fluid transport tube, the guidewire spring and the support member of a fourth embodiment of the present invention.
Figure 8A:
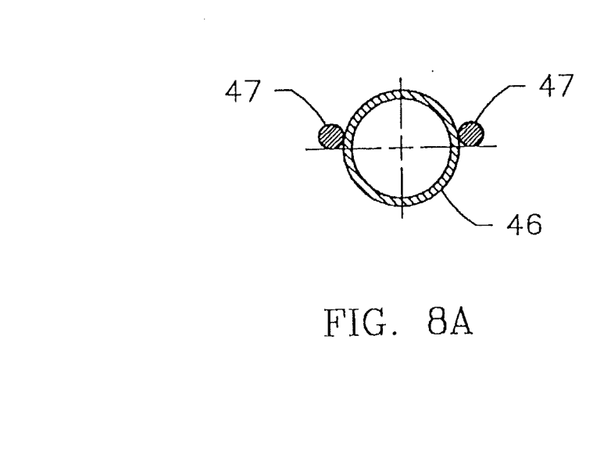
FIG. 8A is a cross-sectional view taken along the lines VIIIA—VIIIA in FIG. 8.
Figure 8B:
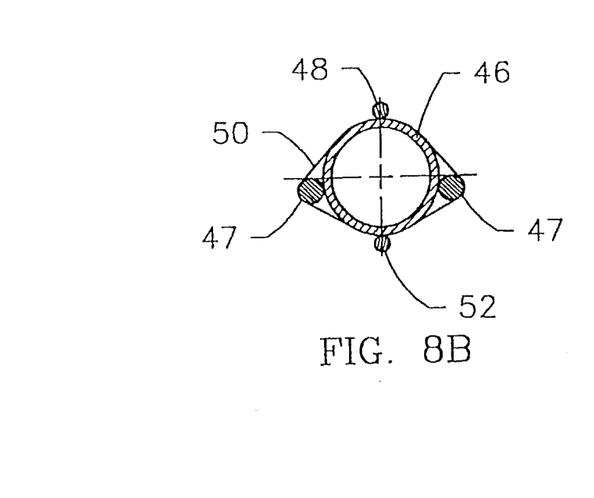
FIG. 8B is a cross-sectional view taken along the lines VIIIB—VIIIB in FIG. 8 and further including the bonding sleeve surrounding the fluid transport tube and the pull cables.

For example, by combining the mounting orientations of the support members 47 to the fluid transport tube 46 shown in FIGS. 7 and 8, the catheter's tip portion 54 can assume various preselected three dimensional curves (i.e., curves existing in more than one plane) when the catheter is used.

Also, although the present invention has been described with reference to a particular catheter handle or operator, other catheter handles may be employed so long as they are able to provide the necessary control of the dual pull cables 48, 52. For example, the rotating and sliding rachet locking mechanism disclosed in U.S. Pat. No. 5,190,050 may be used in place of the helical thread 16 and pin 30 arrangement described hereinabove. Additionally, the pull cables 48, 52 may alternatively be pulled and released by fixing and wrapping them in opposite directions around a pulley or wheel which the user can rotate relative to the handle. Thus, rotation of the wheel in one direction will tighten one pull cable and loosen the other pull cable. Such a pulley or wheel can also be employed if a single pull cable is used. Such a pulley or wheel can also be loaded by a spring or other means which urges the pulley or wheel into a neutral position in which the catheter's tip portion is not curved. An appropriate locking mechanism is preferably included to lock the pulley or wheel into a desired position, thereby locking the catheter's tip portion into a desired curvature.

Additionally, although the steerable catheter of the present invention is expressly disclosed for use in sensing electrical signals in body tissues and/or for applying electric power to such tissues, if this feature is not desired, the catheter design may be readily and suitably modified by eliminating the electrical contact plates 64 in the catheter's distal portion 54, the electrical conductors 62 and the electrical power source or sensor. Similarly, optical fibers can be provided instead of, or in addition to, the electrical conductors 62. In such a modified embodiment one or more optical fibers may be connected to a light source, such as a laser, while one or more other optical fibers are connected to a video camera, light sensor and/or similar viewing or recording devices. Also, a longitudinally movable rigid cable may protrude through a bore or opening in the catheter's distal portion 54 for removal of patient tissue for biopsy. Alternatively, the optical fibers or biopsy instrument may be inserted into the fluid transport tube 46 so that it extends through the catheter's handle to the distal end of the catheter tube 44 and, when or if desired, out of the distal opening 55. Any one or more of these alternative utilities or embodiments may also be combined one with another for a particular use that is contemplated or intended for the catheter of the present invention. In addition, the fluid transport tube 46 may be used to house multiple fluid transport tubes which can each have different uses: for example, one for pumping fluid into the patient, one for pumping fluid out of the patient and one for optics.

Finally, and as should be apparent to those skilled in the art, the dimensions herein described relate to one particular catheter size in the particular embodiment of the inventive apparatus shown in the drawings, and are disclosed solely by way of example and should not, therefore, be understood as an intended limitation on the scope of the invention.

What is claimed is:

1. A tip deflectable, steerable catheter comprising:

a catheter handle having a first body and a second body, said second body being mounted to and for selective movement relative to said first body;

an elongated catheter tube having longitudinally spaced apart proximal and distal ends, said proximal end of said catheter tube being fixedly attached to said first body of said catheter handle;

a catheter distal portion carried at said distal end of said catheter tube and having a distal end most remote from said handle;

an elongated tube having a central lumen disposed therewithin, said elongated tube being disposed within said catheter tube and extending from said proximal end of said catheter tube to said distal end of said catheter distal portion terminating in a distal opening in said catheter distal portion, said elongated tube having an circumferential outer surface;

a pair of elongated support members fixedly attached to and along a length of the circumferential outer surface of said elongated tube, said support members extending within said catheter distal portion and having proximal and distal ends; and a first pull cable having a proximal end and a distal end, said distal end of said first pull cable being fixedly attached to the distal end of said catheter distal portion, and said proximal end of said first pull cable being attached to said second body such that when said second body moves relative to said first body, the distal end of said first pull cable moves longitudinally to cause said catheter distal portion to curve.

2. The tip deflectable, steerable catheter of claim 1, further comprising a second pull cable having a proximal end and a distal end, said distal end of said second pull cable being fixedly attached to the distal end of said catheter distal portion, and said proximal end of said second pull cable being attached to said second body.

3. The tip deflectable, steerable catheter of claim 2, wherein the distal ends of said first and second pull cables are circumferentially spaced apart from one another around the circumferential outer surface of said elongated tube and disposed radially and symmetrically opposite one another relative to said elongated tube.

4. The tip deflectable, steerable catheter of claim 3, wherein the distal ends of said first and second pull cables are disposed around the circumferential outer surface of said elongated tube such that each distal end of each pull cable is circumferentially disposed between only the distal ends of said two support members.

5. The tip deflectable, steerable catheter of claim 1, wherein:

said catheter tube includes a central lumen defined in and extending longitudinally from said proximal end to said distal end of said catheter tube;

said catheter distal portion includes a central lumen defined in and extending longitudinally along said distal portion, said central lumen of said catheter distal portion being aligned with and connected to said central lumen of said catheter tube; and said elongated tube and said first pull cable extending within said central lumen of said catheter tube, and said elongated tube, said first pull cable and said support members extending within said central lumen of said catheter distal portion.

6. The tip deflectable, steerable catheter of claim 1, wherein the proximal ends of said support members are fixedly attached to first body of said handle.

7. The tip deflectable, steerable catheter of claim 1, wherein said support members are circumferentially spaced apart from one another around the circumferential outer surface of said elongated tube.

8. The tip deflectable, steerable catheter of claim 1, wherein at least a portion of a length of each of said support members are attached to said elongated tube in a straight line.

9. The tip deflectable, steerable catheter of claim 1, wherein at least a portion of a length of each of said support members are disposed radially and symmetrically opposite one another relative to and along said elongated tube.

10. The tip deflectable, steerable catheter of claim 9, wherein at least portions of a length of each of said support members form a double helix along said elongated tube.

11. The tip deflectable, steerable catheter of claim 1, wherein at least portions of a length of each of said support members form a double helix along said elongated tube.

12. The tip deflectable, steerable catheter of claim 1, wherein said support members are cylindrical.

13. The tip deflectable, steerable catheter of claim 1, further comprising curvature locking means on said handle and operable for locking the positions of said first and second bodies of said catheter handle and for locking said catheter distal portion in a selected curvature.

14. The tip deflectable, steerable catheter of claim 1, said catheter handle further comprising a curvature straightening means operable for at least partially straightening the curvature of said catheter distal portion.

15. A tip deflectable, steerable catheter comprising:

a catheter handle having a first body and a second body, said second body being mounted to and for selective movement relative to said first body;

an elongated catheter tube having longitudinally spaced apart proximal and distal ends, said proximal end of said catheter tube being fixedly attached to said first body of said catheter handle;

a catheter distal portion carried at said distal end of said catheter tube and having a distal end most remote from said handle;

an elongated tube having a central lumen disposed therewithin, said elongated tube being disposed within said catheter tube and extending from said proximal end of said catheter tube to said distal end of said catheter distal portion terminating in a distal opening in said catheter distal portion, said elongated tube having an circumferential outer surface;

a pair of elongated support members fixedly attached to and along a length of said elongated tube, said support members extending within said catheter distal portion and having proximal and distal ends, said support members being circumferentially spaced apart from one another around the circumferential outer surface of said elongated tube; and a first pull cable having a proximal end and a distal end, said distal end of said first pull cable being fixedly attached to the distal end of said catheter distal portion, and said proximal end of said first pull cable being attached to said second body such that when said second body moves relative to said first body, the distal end of said first pull cable moves longitudinally to cause said catheter distal portion to curve.

16. The tip deflectable, steerable catheter of claim 15, further comprising a second pull cable having a proximal end and a distal end, said distal end of said second pull cable being fixedly attached to the distal end of said catheter distal portion, and said proximal end of said second pull cable being attached to said second body.

17. The tip deflectable, steerable catheter of claim 16, wherein the distal ends of said first and second pull cables are circumferentially spaced apart from one another around the circumferential outer surface of said elongated tube and disposed radially and symmetrically opposite one another relative to said elongated tube.

18. The tip deflectable, steerable catheter of claim 17, wherein the distal ends of said first and second pull cables are disposed around the circumferential outer surface of said elongated tube such that each distal end of each pull cable is circumferentially disposed between only the distal ends of said two support members.

19. The tip deflectable, steerable catheter of claim 15, wherein:

said catheter tube includes a central lumen defined in and extending longitudinally from said proximal end to said distal end of said catheter tube;

said catheter distal portion includes a central lumen defined in and extending longitudinally along said distal portion, said central lumen of said catheter distal portion being aligned with and connected to said central lumen of said catheter tube; and said elongated tube and said first pull cable extending within said central lumen of said catheter tube, and said elongated tube, said first pull cable and said support members extending within said central lumen of said catheter distal portion.

20. The tip deflectable, steerable catheter of claim 15, wherein the proximal ends of said support members are fixedly attached to first body of said handle.

21. The tip deflectable, steerable catheter of claim 15, wherein at least a portion of a length of each of said support members are attached to said elongated tube in a straight line.

22. The tip deflectable, steerable catheter of claim 15, wherein at least a portion of a length of each of said support members are disposed radially and symmetrically opposite one another relative to and along said elongated tube.

23. The tip deflectable, steerable catheter of claim 22, wherein at least portions of a length of each of said support members form a double helix along said elongated tube.

24. The tip deflectable, steerable catheter of claim 15, wherein at least portions of a length of each of said support members form a double helix along said elongated tube.

25. The tip deflectable, steerable catheter of claim 15, wherein said support members are cylindrical.

26. The tip deflectable, steerable catheter of claim 15, further comprising curvature locking means on said handle and operable for locking the positions of said first and second bodies of said catheter handle and for locking said catheter distal portion in a selected curvature.

27. The tip deflectable, steerable catheter of claim 15, said catheter handle further comprising a curvature straightening means operable for at least partially straightening the curvature of said catheter distal portion.

* * * * *